United States Patent
Ayliffe

(10) Patent No.: US 7,417,418 B1
(45) Date of Patent: Aug. 26, 2008

(54) THIN FILM SENSOR

(76) Inventor: Harold E. Ayliffe, 19622 NE. 125th Ct., Woodinville, WA (US) 98077

( * ) Notice: Subject to any disclaimer, the term of this patent is extended or adjusted under 35 U.S.C. 154(b) by 89 days.

(21) Appl. No.: 11/452,583

(22) Filed: Jun. 14, 2006

Related U.S. Application Data

(60) Provisional application No. 60/690,372, filed on Jun. 14, 2005.

(51) Int. Cl.
*G01N 27/00* (2006.01)

(52) U.S. Cl. ............ 324/71.1; 324/688; 204/603; 204/604; 422/68.1

(58) Field of Classification Search ............ 324/71
See application file for complete search history.

(56) References Cited

U.S. PATENT DOCUMENTS

| | | | |
|---|---|---|---|
| 2,656,508 A | 10/1953 | Coulter | |
| 5,126,022 A * | 6/1992 | Soane et al. | 204/458 |
| 5,338,427 A * | 8/1994 | Shartle et al. | 204/604 |
| 5,376,878 A | 12/1994 | Fisher | |
| 5,459,406 A * | 10/1995 | Louge | 324/688 |
| 5,800,690 A * | 9/1998 | Chow et al. | 204/451 |
| 6,045,676 A * | 4/2000 | Mathies et al. | 204/603 |
| 6,169,394 B1 | 1/2001 | Frazier et al. | |
| 6,426,615 B1 | 7/2002 | Mehta | |
| 6,437,551 B1 | 8/2002 | Krulevitch et al. | |
| 6,454,945 B1 | 9/2002 | Weigl et al. | |
| 6,488,896 B2 | 12/2002 | Weigl et al. | |
| 6,638,482 B1 * | 10/2003 | Ackley et al. | 422/68.1 |
| 6,656,431 B2 | 12/2003 | Hall et al. | |
| 6,703,819 B2 | 3/2004 | Gascoyne et al. | |
| 6,794,877 B2 | 9/2004 | Blomberg et al. | |

* cited by examiner

*Primary Examiner*—Vincent Q. Nguyen
*Assistant Examiner*—Benjamin M Baldridge
(74) *Attorney, Agent, or Firm*—Brian C. Trask

(57) ABSTRACT

An electrically operated, particle detecting, or characterizing, sensor structured as a thin film multilayer sandwich. Three or more electrodes are deposited onto thin layers of film, and stacked to form the sandwich. A representative stacking arrangement provides a pair of stimulated electrodes spaced apart from an intermediate measurement electrode by insulating layers of thin film. A fluid conducting channel, having an axis perpendicular to the film layers, provides electrolytic electrical communication between the three electrodes. Contact pads, arranged to permit electrical interrogation of the electrodes by electrical circuitry, are desirably arranged for access to electrical interrogation probes from a single side of the sensor. Certain sensors may be included in single-use, disposable cartridges adapted for analysis by an interrogation platform.

21 Claims, 19 Drawing Sheets

THIN FILM SENSOR

RELATED APPLICATIONS

This application claims the benefit under 35 U.S.C. 119(e) of the filing date of Provisional Application Ser. No. 60/690,372, filed Jun. 14, 2005, for "ELECTRONIC PARTICLE DETECTOR", the disclosure of which is incorporated as a portion of this disclosure as though set forth in its entirety herein.

BACKGROUND

1. Field of the Invention

This invention relates generally to sensors of the type based upon measurable electrical properties. It is particularly directed to an improved thin film sensor for detecting or characterizing small particles that are suspended in a transport fluid.

2. State of the Art

Pioneering work in particle detection by measuring impedance deviation caused by particles flowing through a small aperture between two containers of electrically conductive fluids is disclosed in U.S. Pat. No. 2,656,508 to W. H, Coulter. The inventor's name is now associated with the principle of particles causing a change in electric impedance as they occlude a portion of the aperture. Since publication of his patent, considerable effort has been devoted to developing and refining sensing devices operating under the Coulter principle. Relevant US patents include U.S. Pat. Nos. 5,376,878 to Fisher, 6,703,819 to Gascoyne et al., 6,437,551 to Krulevitch et al., 6,426,615 to Mehta, 6,169,394 to Frazier et al., 6,454,945 and 6,488,896 to Weigl et al., 6,656,431 to Hall et al., and 6,794,877 to Blomberg et al. All of the above-referenced documents are hereby incorporated by reference, as though set forth herein in their entireties, for their disclosures of technology and various sensor arrangements.

BRIEF SUMMARY OF THE INVENTION

This invention provides an electrically operated sensor including a thin film arrangement structured as a multilayer sandwich. An exemplary sensor includes first and second stimulated electrodes that each provide an area disposed in a substantially planar configuration. A first measurement electrode is disposed between, and is spaced apart from, the first and second stimulated electrodes by electrically insulating thin film layers. A first interrogation channel provides a fluid flow path through the first stimulated electrode, first insulating layer, first measurement electrode, second insulating layer, and the second stimulated electrode. The channel permits electrolytic electrical communication between the first stimulated electrode, first measurement electrode, and second stimulated electrode to form a first interrogation zone disposed between the first stimulated electrode and second stimulated electrode. Desirably, the first stimulated electrode and second stimulated electrode reside on layers of the sensor sandwich. Certain embodiments include a stimulated electrode and at least one measurement electrode that are affixed to opposite sides of one insulator layer.

In certain preferred embodiments, a thickness of the first and second insulating layers is less than about 0.01 inches; a characteristic size of the first interrogation channel is between about 2 and 150 microns; and a thickness of each of the first stimulated electrode, first measurement electrode, and second stimulated electrode is sized less than about 100 microns.

A sensor structured according to certain principles of the instant invention may include a second measurement electrode disposed between the first insulating layer and second insulating layer. Such sensor also includes a second interrogation channel providing a fluid flow path through the first stimulated electrode, first insulating layer, second measurement electrode, second insulating layer, and second stimulated electrode. In certain embodiments, the second channel has a characteristic size between about 2 and 150 microns and permits electrolytic electrical communication between the first stimulated electrode, second measurement electrode, and second stimulated electrode to form a second interrogation zone disposed between the first stimulated electrode and second stimulated electrode. Desirably, insulating layers include alignment structure adapted to urge alignment of constituent layers during assembly of the sensor.

Certain sensors may include a plurality of individually addressable measurement electrodes disposed in sandwich relation between the first stimulated electrode and second stimulated electrode. Such plurality of measurement electrodes are substantially electrically independent from each other, and each associated with a cooperating channel, to form a plurality of parallel interrogation zones disposed between the first stimulated electrode and second stimulated electrode. Certain of such sensors are structured and arranged to provide a plurality of sensor zones disposed for parallel interrogation of a fluid sample. Certain of such sensors may be structured and arranged to provide a plurality of sensor zones disposed for serial interrogation of a portion of a fluid sample.

In some preferred sensors, an entrance to an interrogation channel is structured to form a metering aperture. Sometimes, wall structure of the channel is arranged to form a metering aperture. Desirably, the sensor is structured and arranged to permit electrical communication between selected electrodes and cooperating probe structure of an interrogation platform by way of electrical contact pads disposed for access by probe structure from a single side of the sensor. One such sensor includes an electrically conductive via disposed between a contact pad and its associated electrode, with the via passing through at least one insulation layer. It is also within contemplation that the sensor may be structured and arranged to provide access for a probe structure of an interrogation platform, to a connector contact pad associated with an electrode, through a window formed through an insulating layer.

Sensor may be used in combination with a cartridge including a sample input aperture in fluid communication through the sensor to a waste reservoir. Such cartridge is typically configured and arranged to present contact pads associated with the sensor for electrical communication with electrical interrogation circuitry. Desirably, the cartridge is adapted for one-time, disposable use. A cartridge is typically adapted for use with an interrogation platform. Certain operable interrogation platforms include probe structure effective to form an electrical communication between the sensor's electrodes and electronic interrogation circuitry of the platform. Further, the platform may include a motive source to cause fluid transport through the sensor. Desirably, the platform will also include alignment structure to assist in engagement of the cartridge in repeatable and operable position with respect to the platform.

Some sensors may include third and fourth stimulated electrodes, each of which provides an area disposed in a substantially planar configuration. In such case, a second measurement electrode is disposed between the third and fourth stimulated electrodes. A second channel in included to provide a fluid flow path through the third stimulated electrode, first insulating layer, second measurement electrode, second insulating layer, and fourth stimulated electrode, and permits electrolytic electrical communication between the third stimulated electrode, second measurement electrode, and fourth stimulated electrode to form a second interrogation zone associated with the sandwich-like sensor.

The invention contemplates a method for analyzing particles suspended in a fluid, including the steps of: a) adding a known volume of particle-containing fluid to a one-time use disposable cartridge that includes a thin film sensor; b) inserting the cartridge into a docking port of an interrogation platform; c) causing a pressure differential across the thin-film sensor effective to move the particle-containing fluid through the sensor; d) analyzing particles flowing through the sensor by monitoring changes in electric impedance as the particles flow through one or more interrogation channels; and e) displaying analysis results on a display screen of the platform.

BRIEF DESCRIPTION OF THE DRAWINGS

In the drawings, which illustrate what are currently considered to illustrate the best modes for carrying out the invention.

DETAILED DESCRIPTION OF THE ILLUSTRATED EMBODIMENTS

Figure 1:
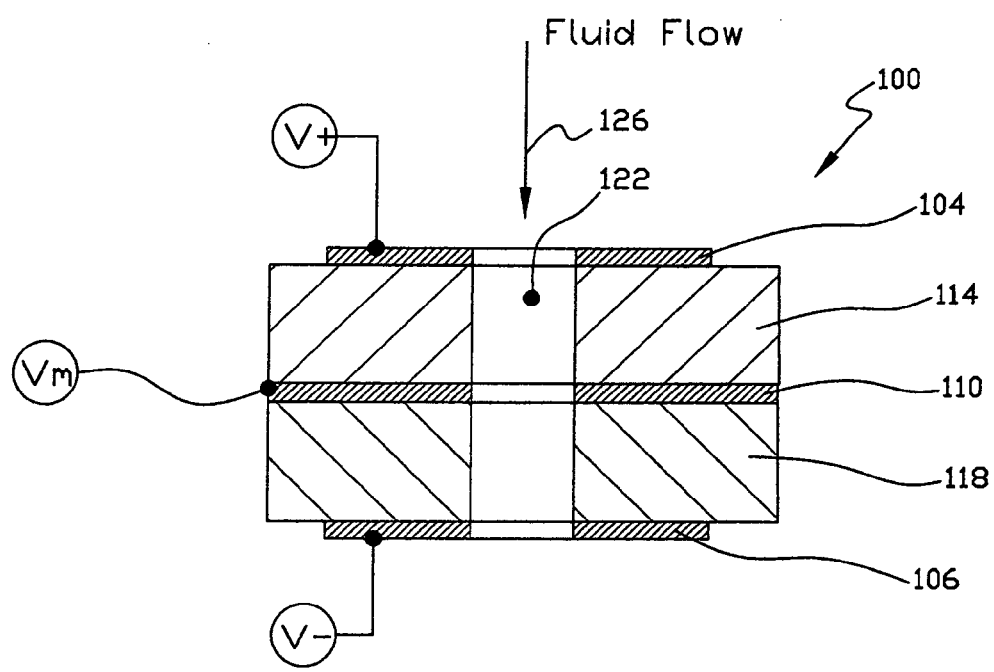
FIG. 1 is a cross-section view taken through a portion of a currently preferred thin film sensor structured according to certain principles of the instant invention.

Reference will now be made to the drawings in which the various elements of the illustrated embodiments will be given numerical designations and in which the invention will be discussed so as to enable one skilled in the art to make and use the invention. It is to be understood that the following description is only exemplary of the principles of the present invention, and should not be viewed as narrowing the claims which follow.

The present invention may be embodied to provide an extremely sensitive, accurate, and low-cost device operable to interrogate certain properties of particle-bearing fluids. Embodiments structured according to principles of the invention may also be used in various purification procedures. Examples of particle-bearing fluids on which the invention may be used to advantage include, without limitation, whole blood, portions of blood including serum, whole milk, and semen samples to obtain a sperm count. In general, the present invention may be used to advantage for those analyses involving numerical evaluation of, or particle size distribution for, a particle-bearing fluid. In one embodiment, an interrogation device structured according to the instant invention may be used to perform a complete blood count (CBC) by discriminating between certain cell morphological types.

Sometimes, devices structured according to the instant invention may be used as a detector device for particles having bound markers, such as latex or magnetic beads. Such markers may operate under some sort of discriminatory mechanism or process (such as antigen-antibody binding), to permit binding with only certain cell types. The attached beads or markers can be used to pull targeted cells out of the blood (or other fluid sample), as a method of purification. The "purified" or concentrated cells can then be counted in an embodiment of the present invention. One such test performed on blood samples is characterized as an absolute CD4+ white blood cell count. The CD4+ white blood cells are white blood cells that express the CD4+ antibody on their membrane and play a key role in the immune system.

For convenience in this disclosure, the invention will generally be described with reference to its use as a particle detector. Such description is not intended to limit the scope of the instant invention in any way. For example, sensors structured according to certain principles of the instant invention may be used to discriminate between cell types, evaluate particle size distributions, or otherwise characterize particles.

Furthermore, for convenience, the term "fluid" may be used herein to encompass a fluid mix including a fluid base formed by one or more diluents and particles of one or more types suspended or otherwise distributed in that fluid base. Currently preferred embodiments of the invention are adapted to interrogate particles found in whole blood samples, and this disclosure is structured accordingly. However, such is not intended to limit, in any way, the application of the invention to other fluids including fluids with particles having larger or smaller sizes.

An exemplary thin film sensor, generally indicated at 100, is illustrated in FIG. 1. Sensor 100 is structured as a thin film sandwich, and includes a first stimulated electrode 104 and a second stimulated electrode 106. A measurement electrode 110 is spaced apart from the first and second stimulated electrodes 104, 106 by first and second electrically insulating layers of thin film, 114 and 118, respectively. The thin film layers substantially isolate the three electrodes and resist electrical communication there-between.

At least one channel 122 is formed through the sandwich to permit fluid flow, indicated by arrow 126, through the sensor 100. As indicated by the double arrows on flow indicator 126, sensors can be disposed in a test circuit for fluid flow through the sensor in either direction. Channel 122 permits electrolytical electric communication between the three electrodes, 104, 110, 106. Such communication permits electrical interrogation of particles traveling along the channel 122. Therefore, sometimes channel 122 is characterized as an interrogation channel. Channel 122 may be structured to inherently form a metering aperture to promote single-file travel of cells or particles.

Typically, the stimulated electrodes 104, 106 receive applied periodic electrical voltage signals of opposite sign $V^+$ and $V^-$, and the induced impedance $V_m$ is monitored at the measurement electrode 110 as particles suspended in a fluid flow through channel 122. $V_m$ may be characterized as the passive resistance measured at electrode 110, and is influenced by the presence of particles in channel 122. The measured signal $V_m$ changes sign as a particle passes the measurement electrode 110, and thereby causes a more distinct measured signal. Such an arrangement dramatically improves signal-to-noise ratio.

It should be noted that, desirably, the electrodes of sensors structured according to certain principles of the instant invention are radially disposed about an axis of the channel 122 to form a circumferentially continuous, axially extending, portion of channel 122. Therefore, the sensor 100 is structured to provide a Coulter-style orifice having an interrogation zone disposed inside the orifice. Furthermore, the magnitude of measured voltage $V_m$ at the measurement electrode 110 due to particle departure from a consistent path along an axis of channel 122 is substantially independent of the actual path of the particle.

Each electrically insulating layer may be formed from any material resistant to conductance of electricity. The insulating layer(s) operates to place electrodes in electric isolation from each other, except for communication along a proscribed fluid path. However, it is currently preferred for the insulators to be formed from flexible, film-like plastic materials, including polyamides and polyesters such as Mylar and Kapton, respectively. Such films in currently preferred sensors are typically on the order of 0.0001 to 0.010 inches (2-200 microns) in thickness, although thinner or thicker materials may be used, as desired for particular applications. Embodiments constructed according to certain principles of the instant invention can be manufactured using virtually any thicknesses for substrate insulators and electrodes, However, thickness of insulator and electrode layers, and channel sizes, in a particular sensor are typically sized in accordance with the intended use of that particular sensor. As non-limiting examples, it is within contemplation to form an alternative insulator layer from nonconductive sheet or plate material, or even from a portion of an electronic circuit board.

Electrodes are generally made from metal or alloys of metals, including Aluminum, Platinum, Gold, Copper, Silver, Chromium, Titanium, and the like, although any other operable electrically conductive material would suffice. It is currently preferred to coat the measurement electrode (and sometimes one or more of the stimulated electrodes), onto an insulator film to improve material handing characteristics during assembly of the sensor. The coating operation may be carried out by electroplating, or using some other known method, such as sputtering or electro-deposition techniques, and the like. It is further within contemplation to incorporate micro-machining methods, such as masking and etching, as well as screen printing techniques and laser etching, to formulate individual electrode structures.

The thickness of electrodes in currently preferred sensors is about 0.25 microns (0.00000984 inches). An operable range of thickness for certain electrodes used in sensors adapted for blood cell detection or characterization is between about 0.05 microns to 100 microns. Sputtered metal layers can be as thin as 10 nanometers (0.010 microns). The stimulated electrodes 104, 106 can be more thin than the measurement electrode 110. Electrodes having reduced thickness are less expensive (generally, depending on metal choice and fabrication choice). The outer electrodes 104, 106 are typically arranged in a test circuit to have a much larger surface area disposed in contact with the sample solutions (which keeps the electrode/electrolyte interface impedance low). A minimum dependable thickness of the measurement electrode 110 is about 1 micron (0.0000393 inches) to provide enough total surface area with the solutions to keep the interface impedance to a reasonable level. However, an operable range of thickness for electrode 110 used for interrogating blood samples is about 0.1 to 100 microns.

It is within contemplation to provide surface coatings on sensors structured according to certain principles of the instant invention to reduce impact from contact with the sensor structure and the fluid passing therethrough. Such coating arrangement can be provided to reduce the clotting cascade in whole blood samples, for example. Coatings operable in sensors for use with such blood samples include Teflon, heparin, and PRO-based materials.

Figure 2:
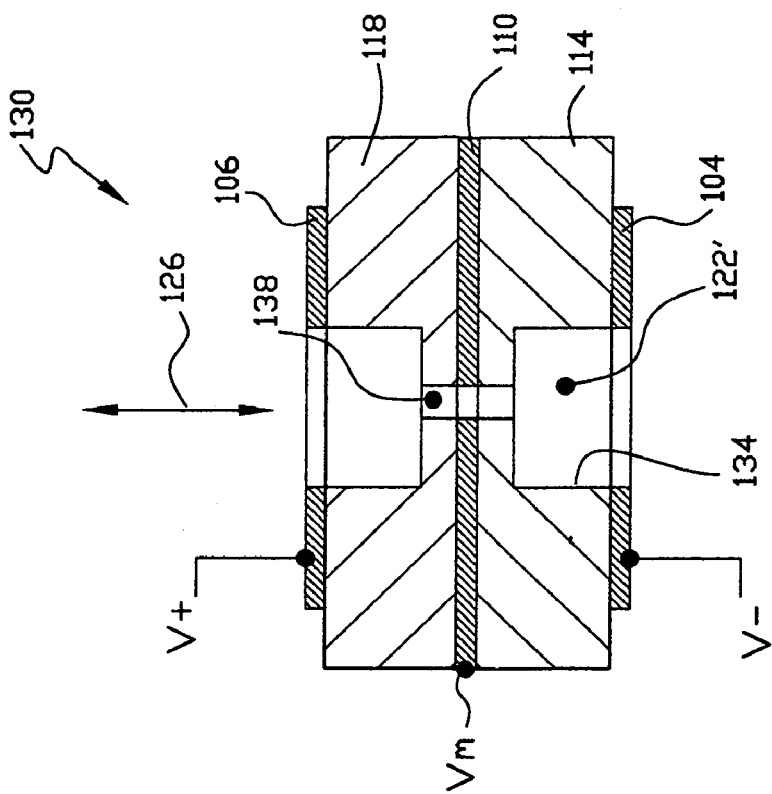
FIG. 2 is a cross-section view taken through a portion of a first alternative embodiment of a thin film sensor.

FIG. 2 illustrates certain construction details of a second sensor, generally indicated at 130. Sensor 130 is structured in substantially the same manner as sensor 100, but includes additional fluid flow metering structure in its channel 122'. As illustrated, walls 134 of channel 122' are arranged to form an aperture 138 of reduced size compared to the rest of channel 122'.

Figure 3:
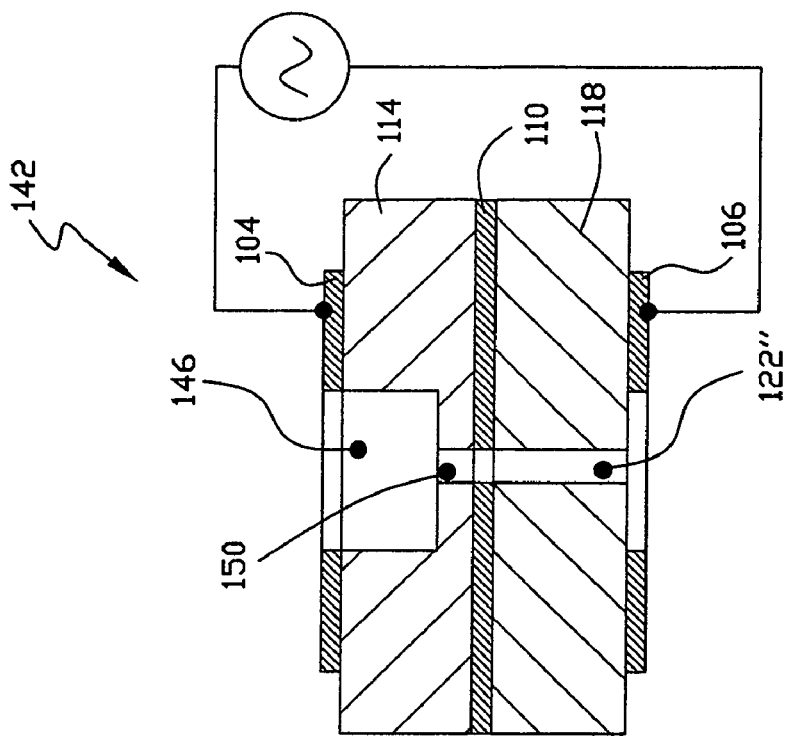
FIG. 3 is a cross-section view taken through a portion of a second alternative embodiment of a thin film sensor.

FIG. 3 illustrates certain construction details of a third sensor, generally indicated at 142. Sensor 142 is similar to sensor 130, but has a different arrangement of metering structure associated with interrogation channel 122". Channel 122" includes a larger size opening 146 disposed on one side of the sensor 142, with a reduced size portion 150 of channel 122" forming a metering aperture closer to the measurement electrode 110. As will be apparent, the structure of a channel 122 may be arranged as desired to form a desired particle flow condition.

For devices structured to interrogate particles in the currently preferred small size ranges, the interrogation channel 122 may be formed, before or after stacking the layers of a sensor sandwich, using micro-machining techniques, such as laser drilling or plasma etching techniques, and the like. Particles in the currently contemplated "small" sizes range between about 2-150 microns. Larger devices constructed according to certain principles of the invention may simply be drilled with conventional mechanical machining methods, including drilling, or with water jet or laser cutting. In devices adapted to perform a complete blood count (CBC) test, the size of an interrogation channel may be somewhere around 10-40 micrometers (in diameter, for a channel having a substantially round cross-section). Preferably, the channel size is about 10 μm for a counting red blood cells in the CBC, and about 35-40 µm for counting white blood cells in the CBC. In a device adapted to perform a CD4+ test, the channel may have a size of about 35 micrometers. In reference to "size" of a channel, a characteristic size is intended. When the channel 122 has an approximately round cross-section, such characteristic size corresponds to the average diameter of the cross-section. Of course, channels having non-round cross-sections are within contemplation, for example, rectangular, oval, and other shapes that may be formed during manufacture of the device.

Figure 5:
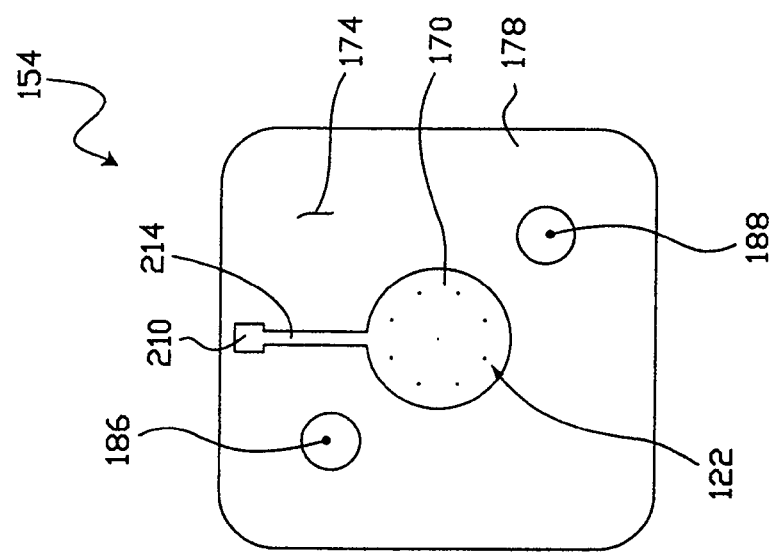
FIG. 5 is a bottom view of the sensor illustrated in FIG. 4.
Figure 4:
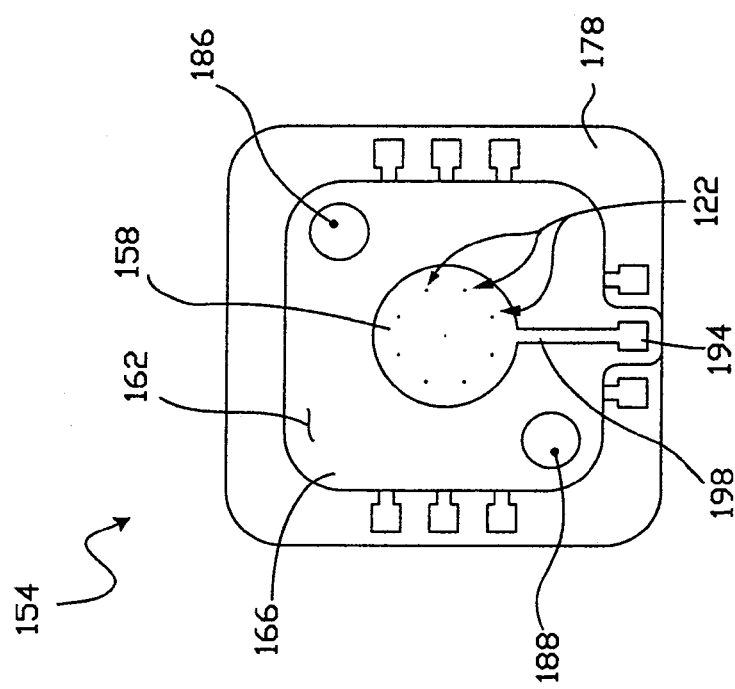
FIG. 4 is a top view of a first currently preferred sensor structured according to certain principles of the instant invention.
Figure 6:
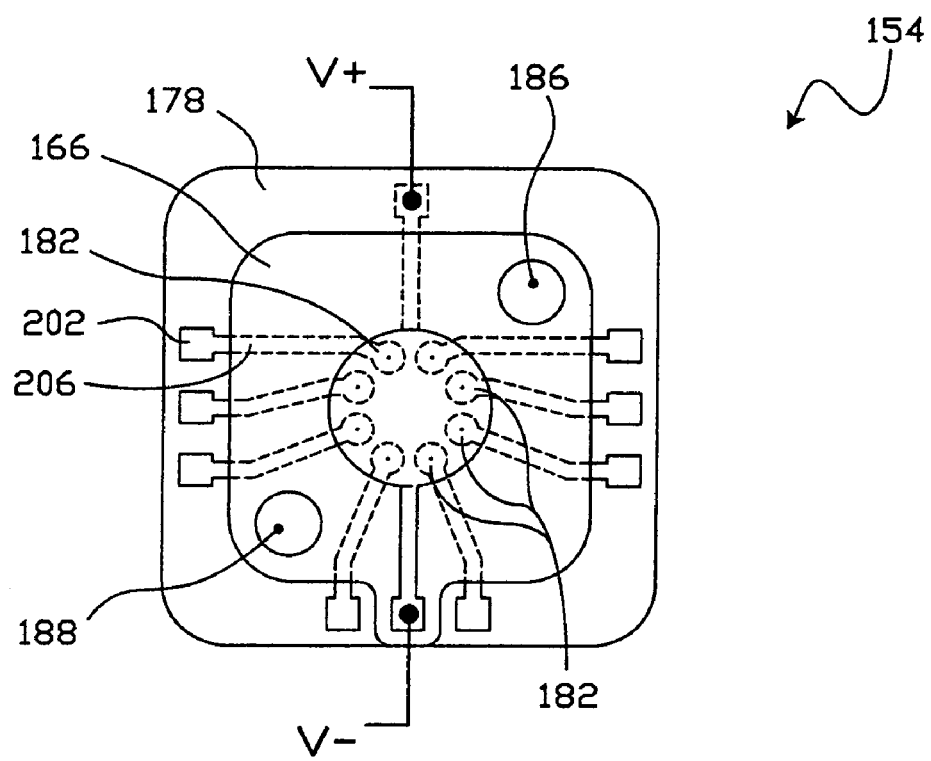
FIG. 6 is the same view as FIG. 4, but with internal components also illustrated.

FIGS. 4-6 illustrate a first currently preferred embodiment of a sensor, generally indicated at 154, structured in accordance with certain principles of the instant invention. Sensor 154 is constructed as a multilayer sandwich, including thin film insulation layers spacing apart electrodes. A first stimulated electrode 158 is carried on top surface 162 of top thin film layer 166. A second stimulated electrode 170 is carried on bottom surface 174 of bottom thin film layer 178. One or more measurement, or interrogation electrode 182 is disposed between the top and bottom thin film layers, 166 and 178, respectively. A channel 122 passes through each measurement electrode 182, the first stimulated electrode 158, the second stimulated electrode 170, and the intervening film layers 166 and 178. Eight measurement electrodes 182 are illustrated in FIG. 6. Therefore, sensor 154 provides eight independent sensing channels 122 available for simultaneous parallel analysis of a fluid sample passing through the sensor 154.

It is currently contemplated to manufacture sensors, such as sensor 154, with up to 200, or more, of such parallel channels. Any number of interrogation channels may be provided, numbering from one to as many as desired, up to a limit imposed by manufacturing or data acquisition considerations. In any case, it is currently preferred to form the channel 122 to provide a continuous stretch of electrode material disposed as a ring section of the channel. Such an encircling electrode configuration tends to average out the signal produced in the measurement electrode, substantially regardless of the relative position of an undersize particle with respect to the channel centerline.

With reference still to FIGS. 4-6, it is currently preferred to provide alignment features, such as the illustrated holes 186, 188, to assist in alignment of the constituent structures as respective layers forming the device are "stacked" on one another. Such alignment features permit the manufacturing process to be automated using conventional reel-to-reel manufacturing techniques. Individual sensors may then be "sliced and diced" from the reel of product. The illustrated spaced-apart holes are only one sort of workable alignment feature within contemplation. Any arrangement of structure operable to align the layers and components may be used.

The stacked components of a sensor form a sandwich assembly that may be regarded as a "chip". Chips can range in size from large to small, with a preferred chip being relatively small, at perhaps about ½cm². Certain preferred embodiments of the chip form a micro-electro-mechanical system, which may therefore sometimes also be called a MEMS chip. The chip is then typically assembled as a component in a device that may be characterized as a "cartridge" adapted to interface with interrogation electronics. Preferably, the cartridge is sufficiently low cost as be regarded as disposable, even subsequent to only one use. While a single interrogation "layer", or sandwich, is illustrated, it is within contemplation to form chips having a plurality of stacked interrogation layers, to provide a plurality of interrogation electrodes arranged along an axis of the interrogation channel 122.

With continued reference to FIGS. 4-6, it is desirable to include contact pads arranged at convenient and operable locations to receive probe structure of an interrogation circuitry, effective to place each such probe structure into separately addressable communication with a selected electrode. For example, contact pad 194 is placed into electrical communication with electrode 158 through lead element 198. Similarly, contact pad 202 communicates with an electrode 182 through electrically conductive lead element 206. Contact pad 210, disposed on the bottom of layer 178, is in electrical communication with electrode 170 by way of lead element 214. Typically, contact pads and lead elements are formed during the deposition or coating process that forms the corresponding electrode.

Figure 7:
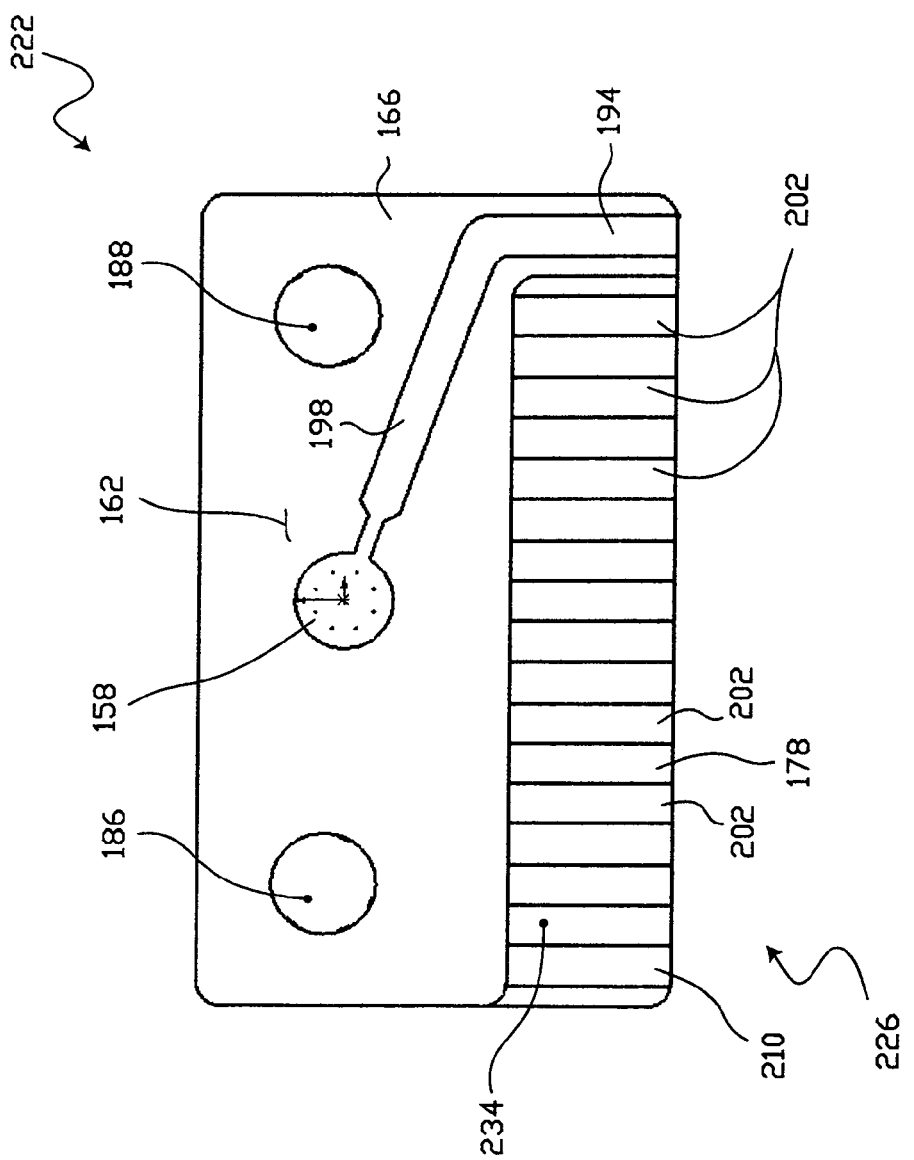
FIG. 7 is a top view of a second thin film sensor structured according to certain principles of the instant invention.
Figure 8:
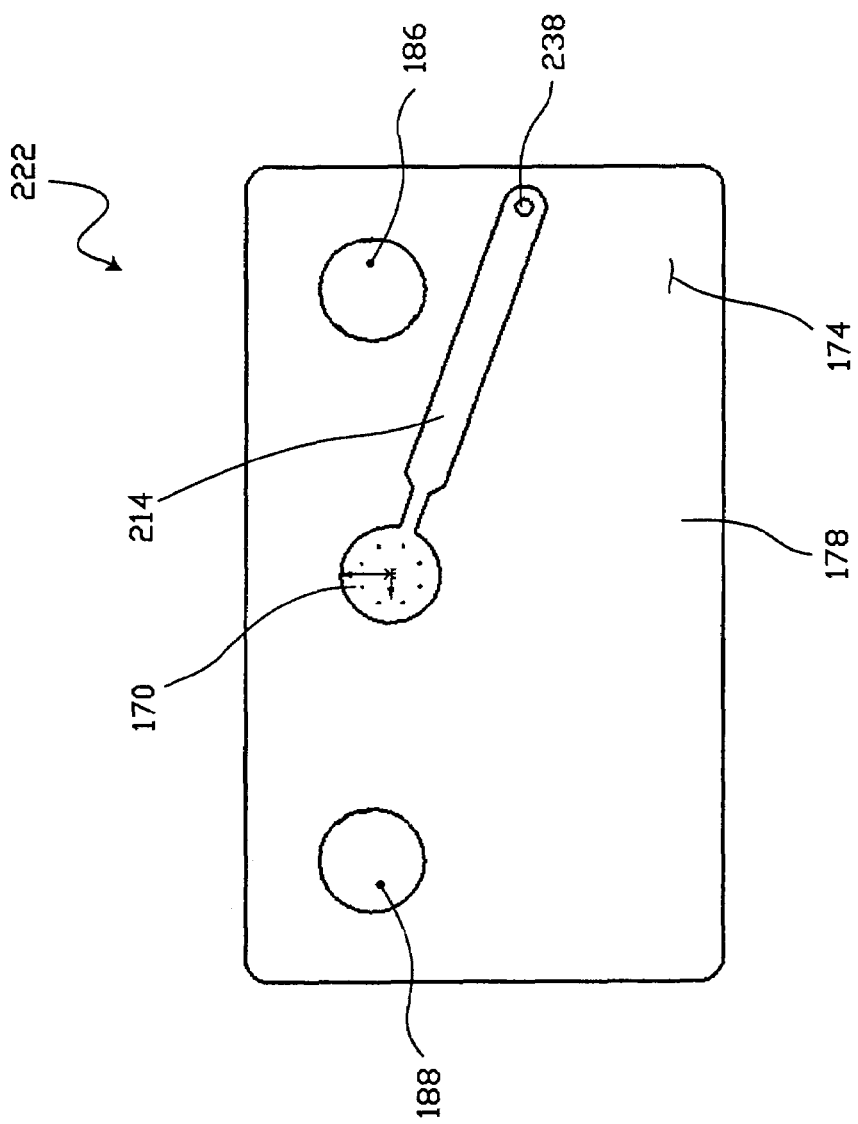
FIG. 8 is a bottom view of the sensor illustrated in FIG. 7.
Figure 9:
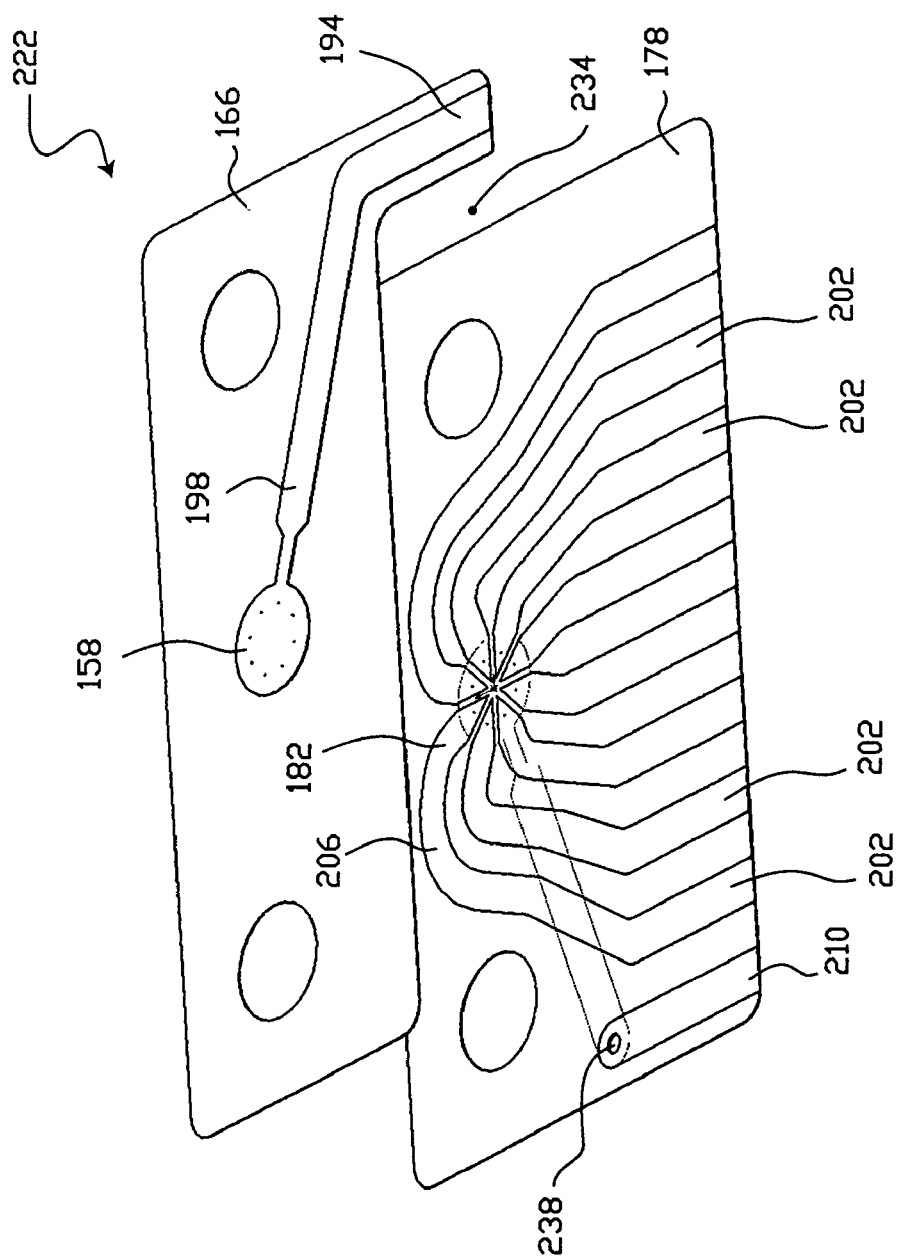
FIG. 9 is an exploded assembly view from above and in perspective of the sensor of FIG. 7.

The preferred embodiment 222, illustrated in FIGS. 7-9, is configured to locate all of the electrical probe contact pads, generally indicated at 226, for access by probe structure from a single side of the sensor 222. Alignment features 186, 188 may be provided to assist in manufacturing to locate the various components in a correct, stacked position.

Sensor 222 provides a plurality of sensing channels 122 disposed for parallel analysis of fluid passing through the sensor. Similar to the embodiment illustrated in FIGS. 4-6, sensor 222 includes a common stimulated electrode 158 disposed on top of the sensor. Electrode 158, carried on top surface 162 of top insulator layer 166, is connected to top-mounted contact pad 194 by way of lead element 198.

A plurality of measurement contact pads 202 are each in electrical communication with an associated measurement electrode 182 by way of respective lead elements 206. Again, eight measurement electrodes 182 are illustrated, each such electrode being associated with an interrogation channel 122. Direct access for interrogating probe elements to permit electrical communication with contact pads 202 from the top side of sensor 222 is provided through a window 234 formed in top insulating layer 166.

With particular reference to FIGS. 8 and 9, the common bottom stimulated electrode 170 is carried on bottom surface 174 of insulating layer 178. A via 238 is provided in layer 178 to communicate an electric signal from electrode 170, through layer 178, and to contact pad 210 by way of lead element 214. Therefore, contact pad 210 is also accessible from the top side of the sensor 222 by a probe passing through window 234. Typically, both sides of insulating layer 178 are coated with a patterned electrically conductive material to form the electrodes and lead elements, and to ensure the via 238 forms an electrically conductive portion of the path between contact pad and electrode.

Figure 10:
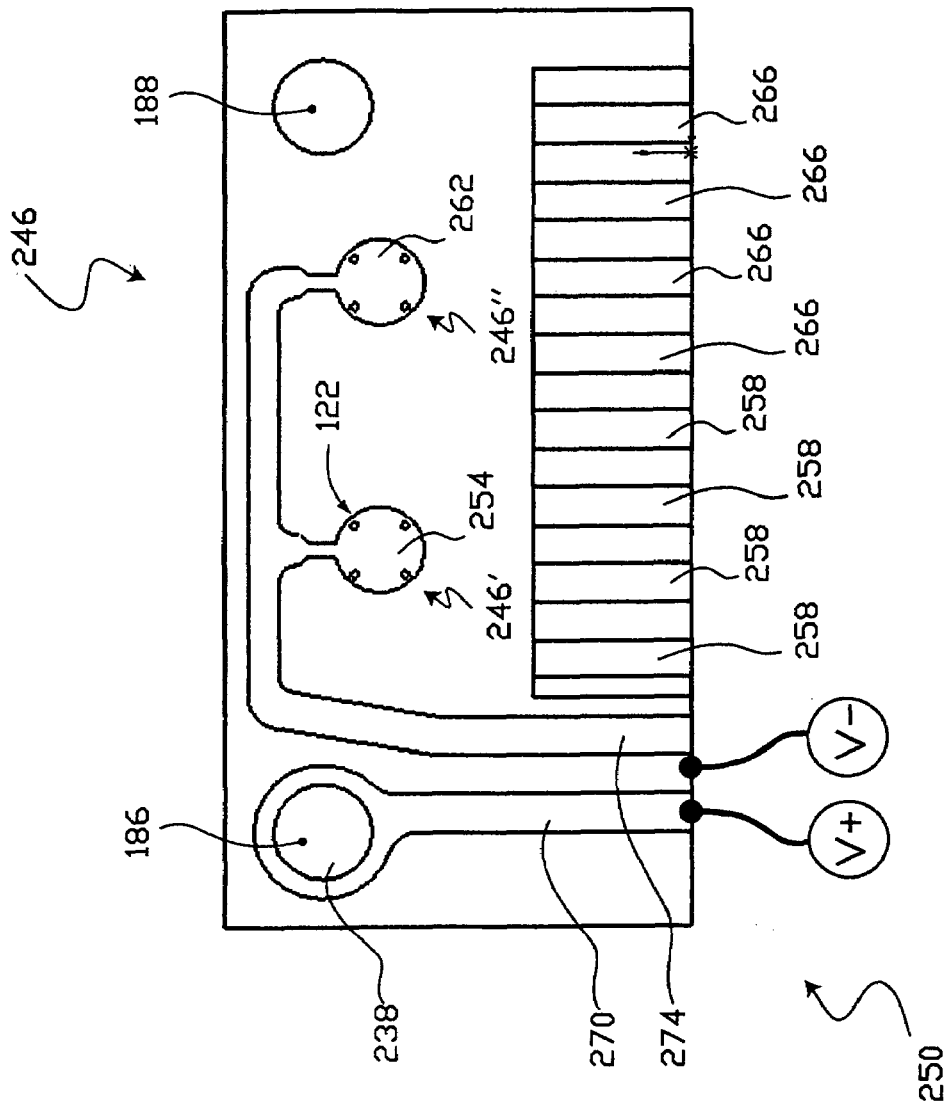
FIG. 10 is a top view of a third thin film sensor structured according to certain principles of the instant invention.
Figure 11:
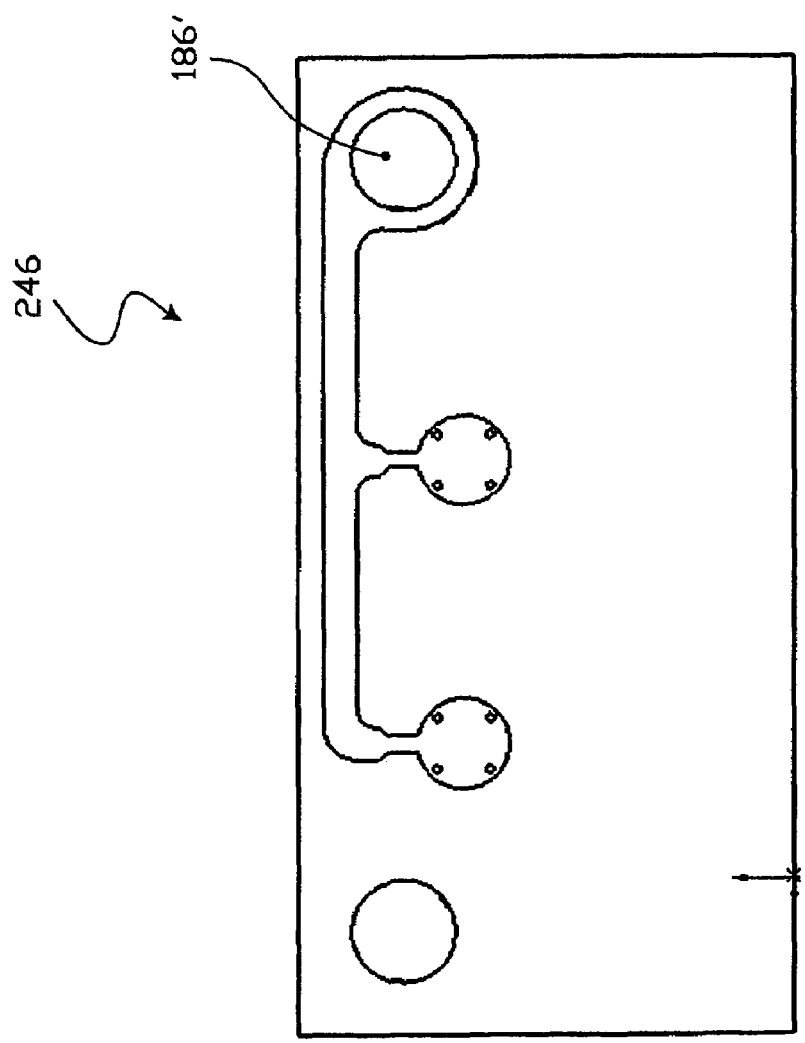
FIG. 11 is a bottom view of the sensor of FIG. 10.
Figure 12:
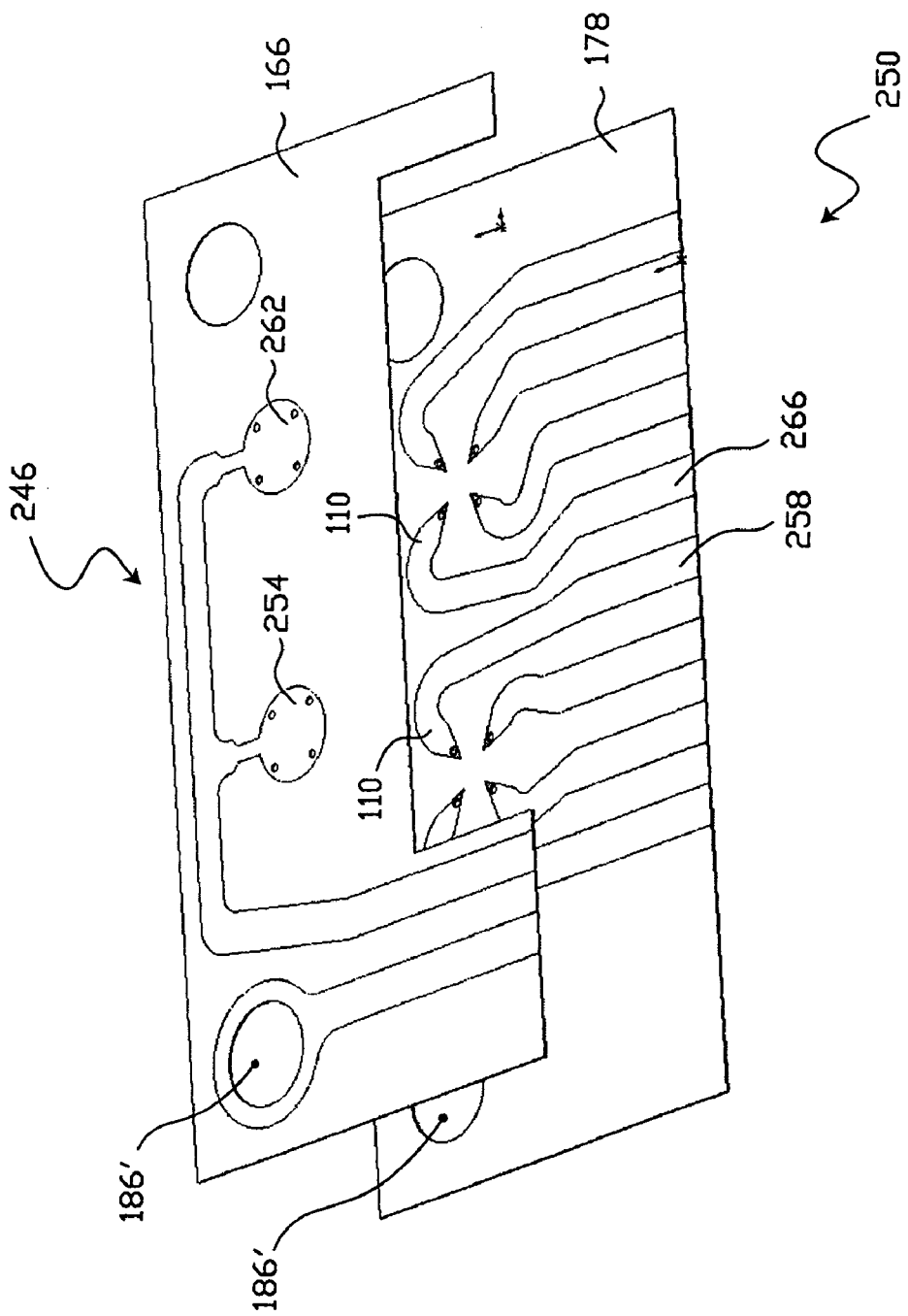
FIG. 12 is an exploded assembly view from above and in perspective of the sensor of FIG. 10.

FIGS. 10-12 illustrate another preferred embodiment structured according to certain principles of the instant invention, generally indicated at 246. Sensor 246 is also configured to provide access for probe elements to all sensor electrodes from one side of the sensor by way of the plurality of contact pads generally indicated at 250. In the illustrated example, alignment structure 186' also serves as a portion of an electrically conductive via 238.

One notable feature of sensor 246 is the presence of pairs of common stimulated electrodes that are spaced apart. Such feature permits flexibility in analysis by permitting cartridge structure to direct fluid flow to either or both stimulated electrodes in any order. In the simplest case, fluid simply is permitted to flow (e.g. top-down) through all interrogation channels of the sensor in parallel simultaneous flow.

Because the common stimulated electrodes are spaced apart, fluid flow through the sensor may be manipulated so that different sequential analysis may be performed on the same fluid sample. In such case, the sensor 246 forms a pair of first and second sensors, generally indicated at 246' and 246".

For example, a portion of sample fluid can be directed to flow through the interrogation channels 122 passing through first stimulated electrode 254 for analysis of the signal measured at corresponding measurement electrodes 110 disposed in electrical communication with contact pads 258. A second portion of fluid can then be interrogated by flow past second stimulated electrode 262 and its associated measurement electrodes 110 that are disposed in electrical communication with probe contact pads 266. As nonlimiting examples suggesting different possible analyses, different magnitude or frequency signals $V^+$, $V^-$, may be applied to the stimulated contact pads, 270 and 274 respectively, during each portion of fluid flow.

Notably, the first and second portions of fluid could flow through sensor 246 from either side of the sensor 246. Therefore, subsequent to its analysis by subsensor 246', the first portion of fluid may be manipulated (e.g. to concentrate, remove, or sort particles), and then conveniently be directed to flow through the second subsensor 246".

Figure 13:
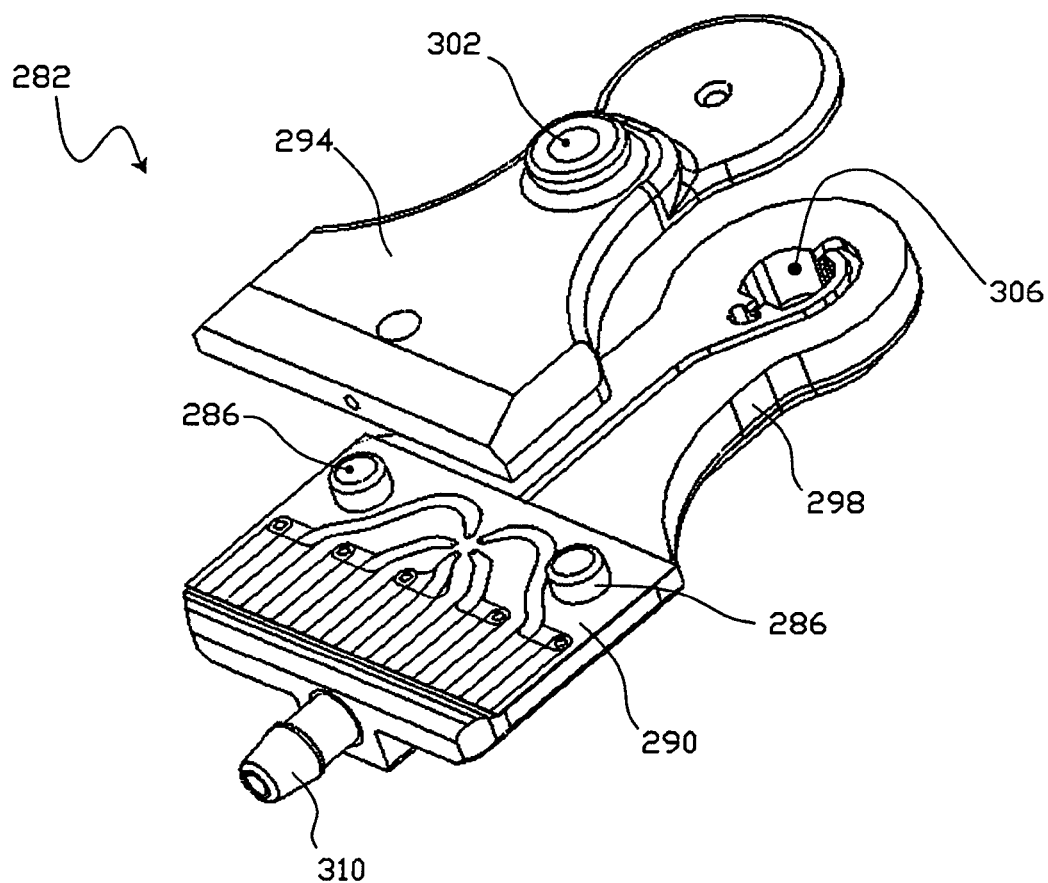
FIG. 13 is a view in perspective of an exemplary cartridge in which a sensor structured according to certain principles of the instant invention may be contained.

Sensors structured according to certain principles of the instant invention may be used to advantage in association with a cartridge adapted to hold the sensor to interface with an interrogation platform to perform an analysis. Currently preferred cartridges are inexpensive, and may be discarded subsequent to a single use. An exemplary cartridge to hold a sensor for particle analysis is generally indicated at 282 in FIG. 13. Cartridge 282 includes alignment pins 286 configured to interface with alignment structure 186 and 188 (e.g. see FIG. 7), to place contact pads 250 in repeatable and reliable position for probe contact. A sensor, such as illustrated sensor 290, can then be precisely located inside an assembled cartridge.

Cartridge 282 includes a top 294, and a bottom 298, which are typically injection molded from plastic, or plastic-like, materials. Top 294 typically includes a sample entrance port 302 disposed in fluid communication through sensor 290 to a sample waste port 306. The sample entrance port may also introduce the sample into an input reservoir disposed upstream of the sensor. The input reservoir may contain various fluids or treatments for conditioning the fluid sample. Desirably, all sample fluid added to the cartridge is confined to, and contained in, the cartridge 282 subsequent to performing a test. A two-sided adhesive film makes an operable connection between top and bottom 298, and forms a fluid barrier to direct fluid through the sensor. An interface structure, such as nipple 310, is provided to permit an interrogation platform to urge fluid flow through the cartridge. Typically, positive or negative pressure is used to urge fluid flow through a cartridge.

As previously made reference to, certain devices constructed according to the invention may include additional factors, such as diluents, solvents, or inhibitors of various kinds, that may be pre-loaded in operable position to interact with an introduced fluid/particle mix prior to interrogating that mix. Such reservoirs may be embodied as a component of a cartridge, or part of a chip.

In the case of a sensor structured as a particle detector, a reservoir holding saline can sometimes be arranged to mix, typically at the start of a CBC or CD4+ test, with an introduced whole blood sample. The saline may further include a blood anticoagulant (e.g. EDTA or Heparin), to resist blood clot formation in the MEMS sensor chip. After passing through an optional pre-filter, the thinned or modified whole blood flows through the microchannel and past the interrogation electrode disposed to permit direct interrogation of the fluid sample portion that is disposed inside the microchannel and between one or more pairs of electrodes.

Figure 14:
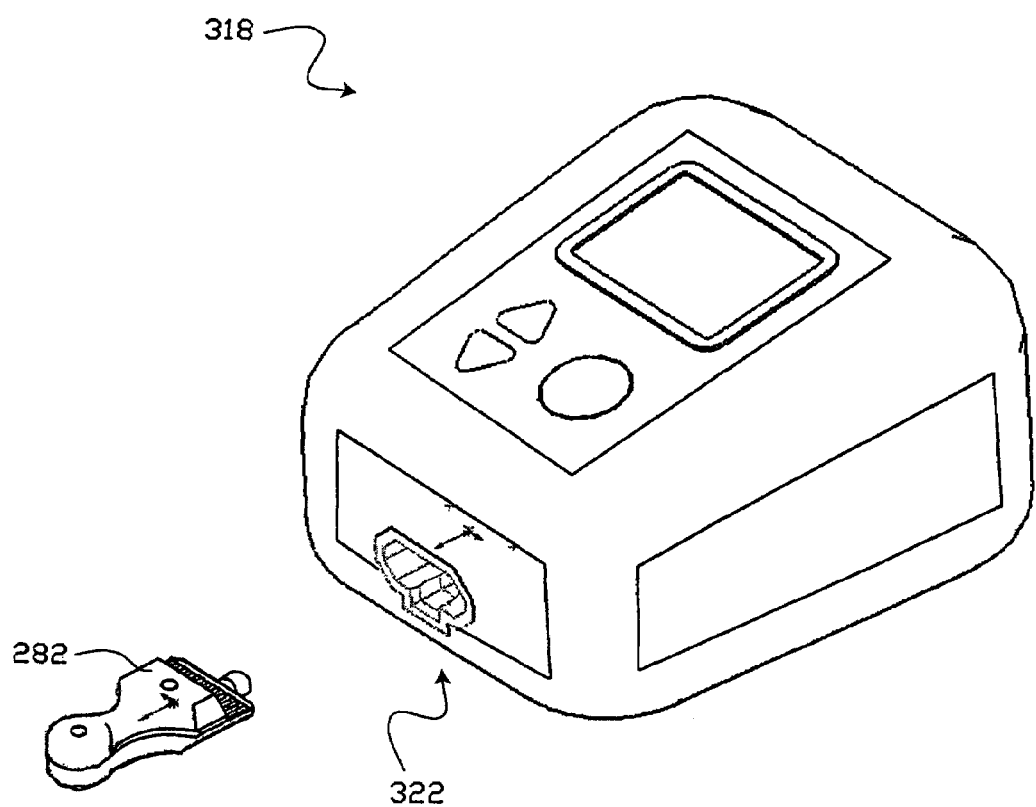
FIG. 14 is a view in perspective of a workable interrogation platform prior to insertion of the cartridge of FIG. 13.
Figure 15:
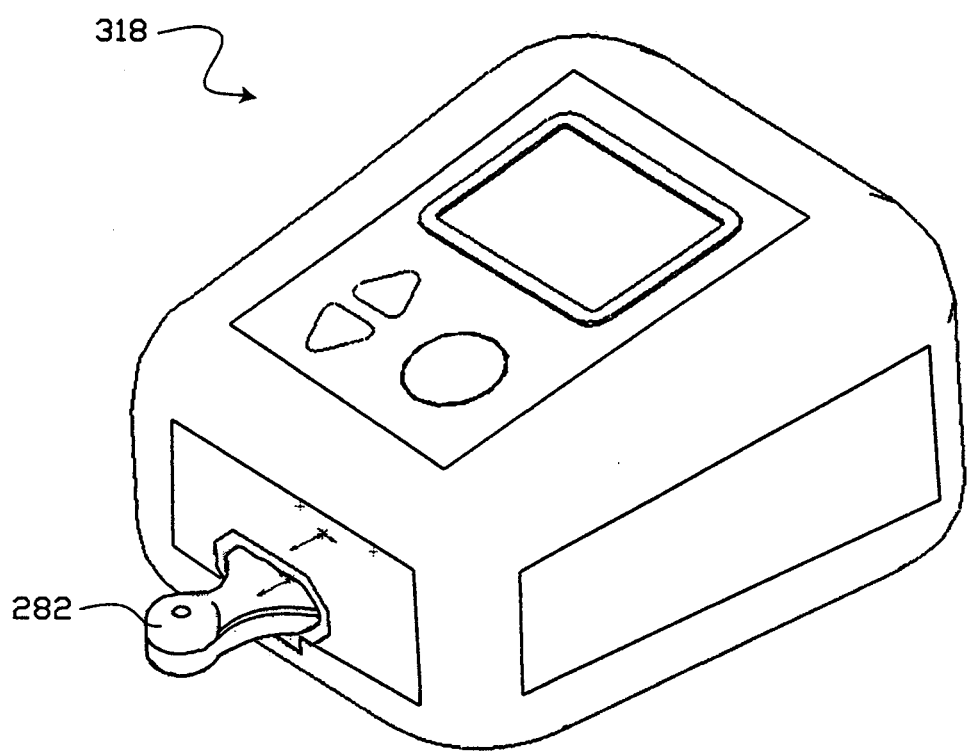
FIG. 15 is a view in perspective of the interrogation platform of FIG. 14, with the cartridge in reception for interrogation.

One exemplary interrogation platform is illustrated in FIGS. 14 and 15, and generally indicated at 318. Desirably, the interrogation platform includes orienting structure, generally indicated at 322, to assist in installing a cartridge, such as illustrated cartridge 282, in a correct and repeatable orientation. Sensors illustrated in this disclosure include contact pads, such as pads 250 in FIG. 10, that are adapted upon installation into a platform 318 to interface with electric probes of a commercially available connector sold by Samtec USA, 1-800-SAMTEC-9, under part No: SIB-110-02-F-S.

One preferred embodiment structured according to certain principles of the instant invention forms a simple particle counter used to count homogeneous solutions of cells in research settings. In such case, a known volume of the cell solution is added to the input reservoir. A disposable cartridge is connected to the interrogation platform, thereby making electrical and pneumatic contact. The count may start automatically or via the push of a button. Positive or negative pressure applied to the cartridge interface structure starts the flow of ionic solution (containing cells). Cells flow through the thin-film sensor using multiple detection channels (from one side to the other of the sensor). All fluids will be stored within the disposable cartridge. Results may be displayed by the platform as cells/volume.

Steps of a method of use of an embodiment structured according to principles of the instant invention may be set forth as:

1. Add a known or pre-measured volume of particle-containing sample fluid to a one-time use disposable cartridge that includes a thin film sensor structured according to certain principles of the instant invention.

2. Insert the cartridge into a docking port of an interrogation platform (Note, steps #1 and 2 could be interchangeable in order).

3. Press start button . . . this causes pressure differential across thin-film sensor to move the fluid sample through the sensor. Simply inserting the cartridge can also be used as an impetus operable to start an analysis.

4. Analyze particles flowing through the sensor (in parallel or with single hole sensor) by monitoring changes in electric impedance as the particles flow through one or more interrogation channels. (The simplest analysis might be to monitor relative changes in voltage and count "particles" that exceed a preset threshold voltage).

5. Display results of the analysis on platform's screen (e.g. in units of particles per volume such as cells/microliter).

6. Remove and dispose of cartridge. The fluid solution is desirably contained within the cartridge to reduce risk of infection or spread of disease.

Figure 16:
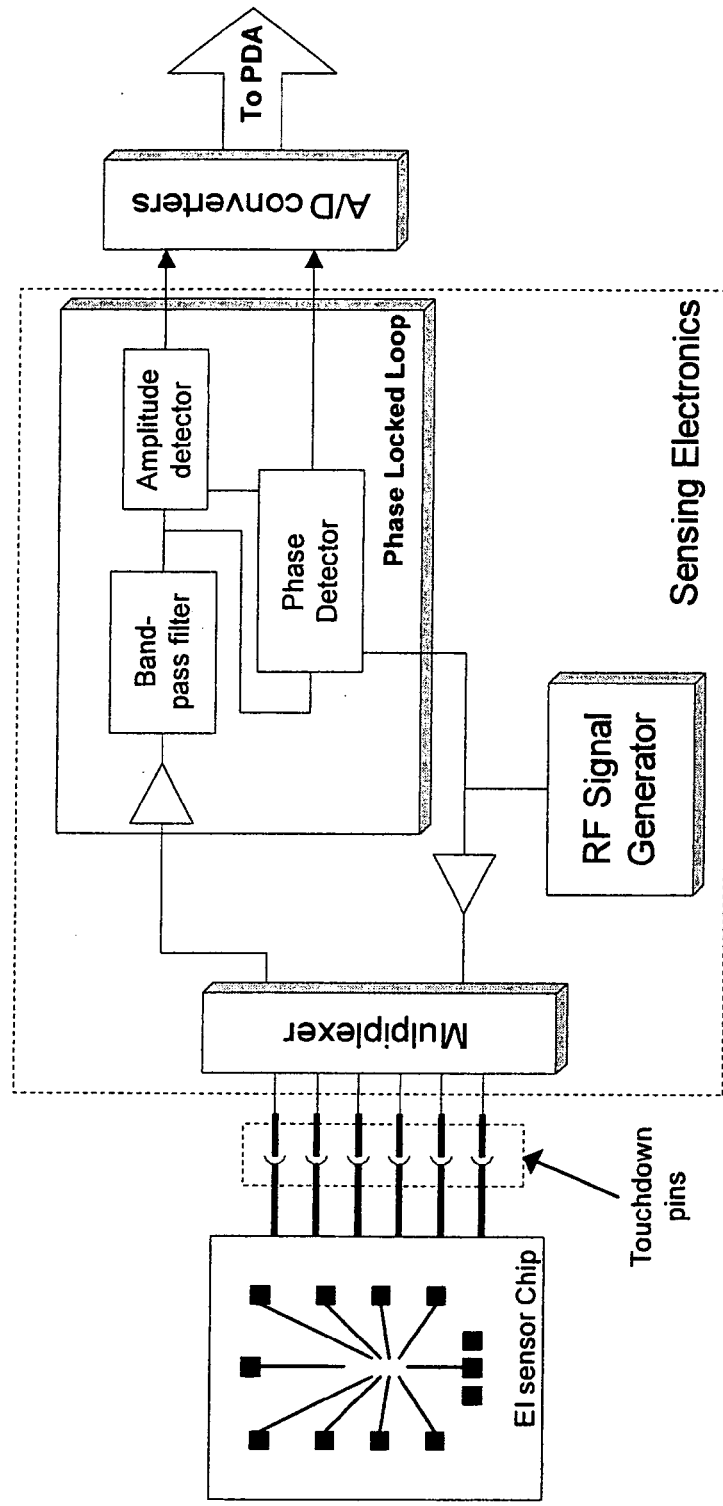
FIG. 16 is a schematic representation of a first exemplary interrogation circuitry for use in an interrogation platform.
Figure 17:
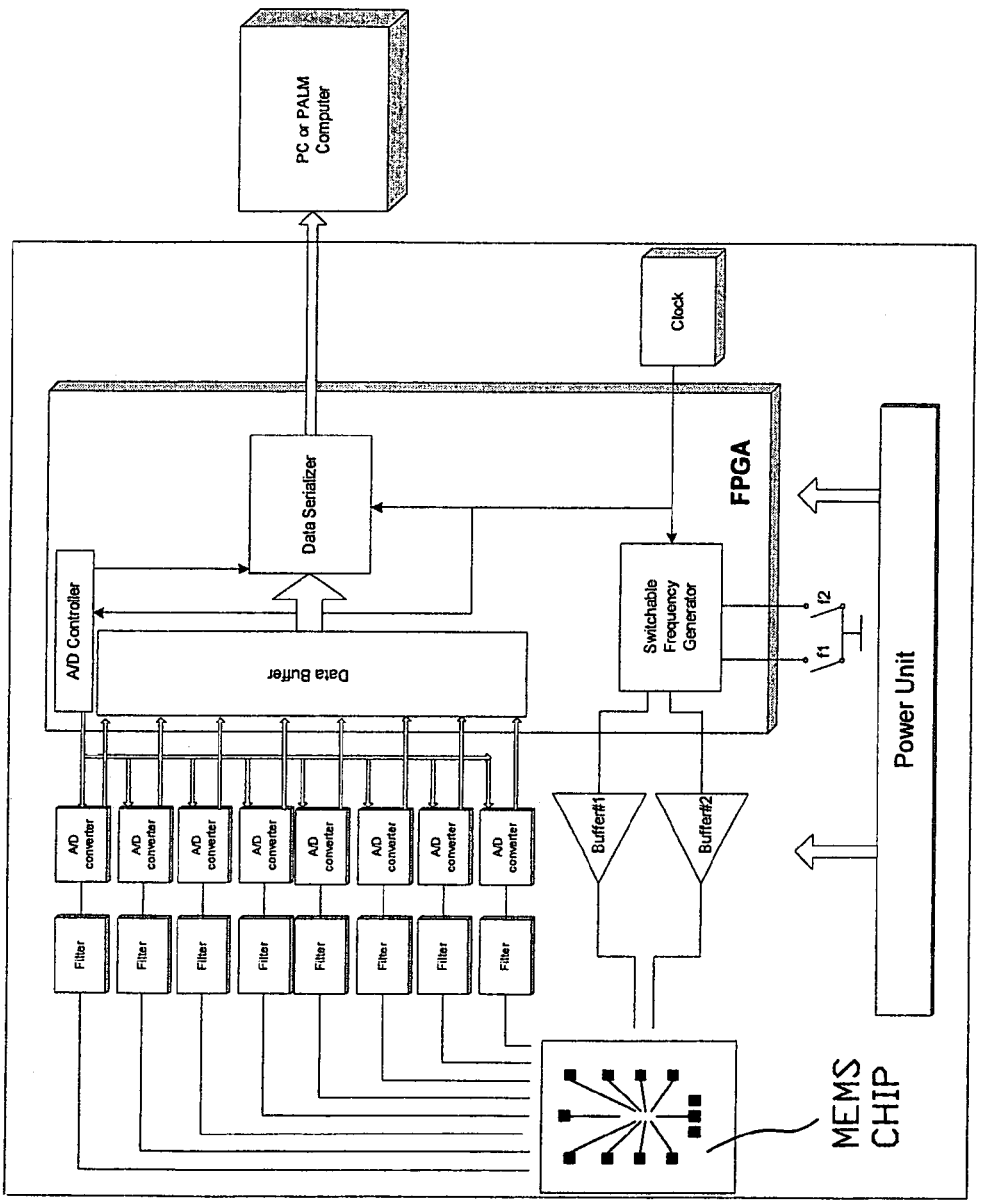
FIG. 17 is a schematic representation of a second exemplary interrogation circuitry for use in an interrogation platform.

FIGS. 16 and 17 illustrate examples of workable interrogation circuitry operable to interrogate preferred sensors. Such circuitry desirably is included in an interrogation platform configured to couple with a cartridge containing a thin film sensor. The touch-down pins illustrated in FIG. 16 are illustrative of the previously mentioned Samtec connector, although many connectors of various configurations are available and also workable.

Figure 18:
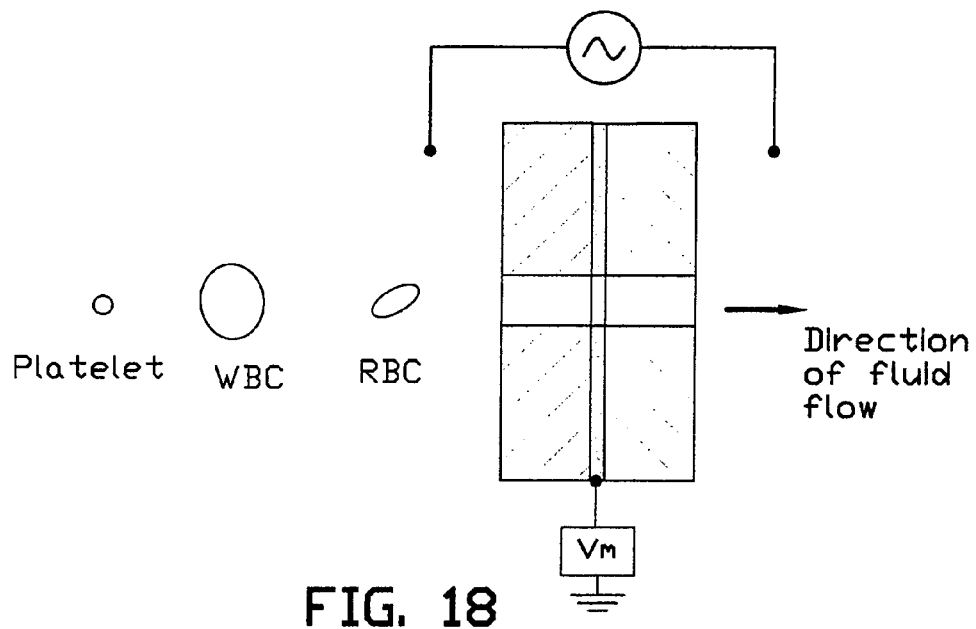
FIG. 18 is a schematic side view of various particles and a sensor.
Figure 19:
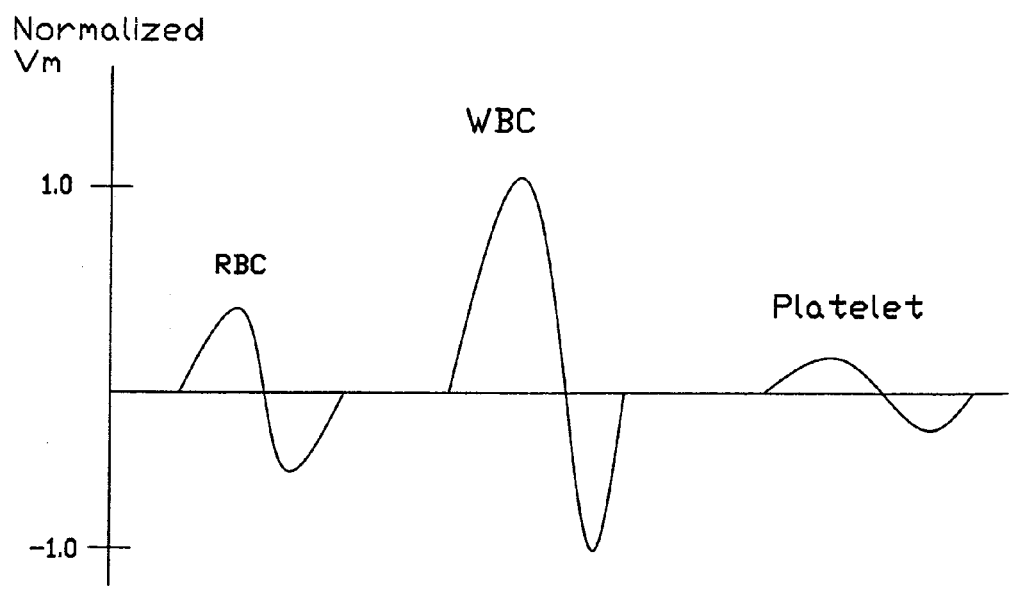
FIG. 19 is a plot illustrating data collected by electrical interrogation of the sensor of FIG. 18 as the illustrated particles pass by the sensor measurement electrode.

FIGS. 18 and 19 illustrate an experimental set up structured according to certain principles of the invention, and data corresponding to the illustrated arrangement, respectively. FIG. 18 depicts three particles, blood cells of different types, prepared to travel in succession through an interrogation channel embodied in a thin film chip structured according to principles of the instant invention. The illustrated channel is about 40 micrometers in diameter, and can be between about 4 to about 400 micrometers in length, in devices structured to interrogate a fluid/particle mix such as found in whole blood. In such devices, the channel diameter can range between about 3 to about 150 micrometers, or so. The data shown in FIG. 19 assume an approximately constant and uniform travel velocity of the particles through the channel. The red blood cell (RBC) is smaller than the channel diameter, but produces a distinctive signal. The white blood cell (WBC) is larger, and causes a large change in voltage. The platelet, being of much smaller size, causes a lesser, albeit a distinct and discernable, signal. The measured voltage signal may be characterized as being proportional to the particle size.

Figure 20:
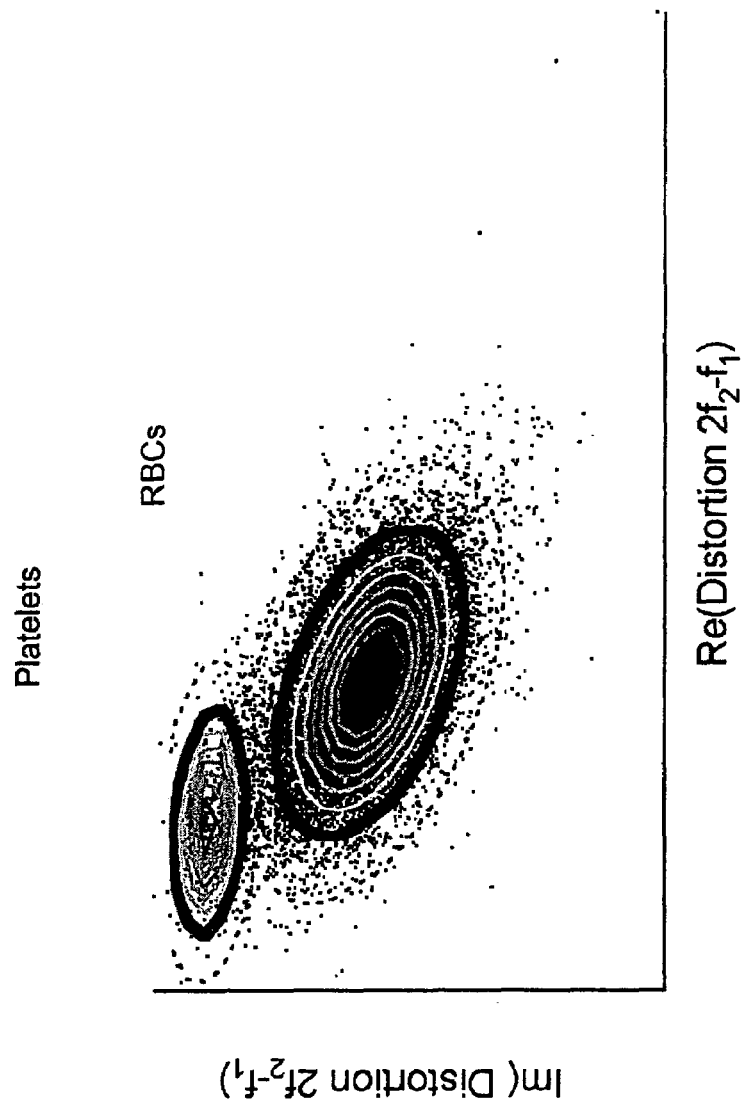
FIG. 20 is a plot illustrating real and imaginary components of electrical impedance measured using a sensor structured according to certain principles of the instant invention.

FIG. 20 illustrates real and imaginary portion of impedance signals recordable from certain embodiments of the invention. As illustrated, cell types may be differentiated based upon such evaluation.

Figure 21:
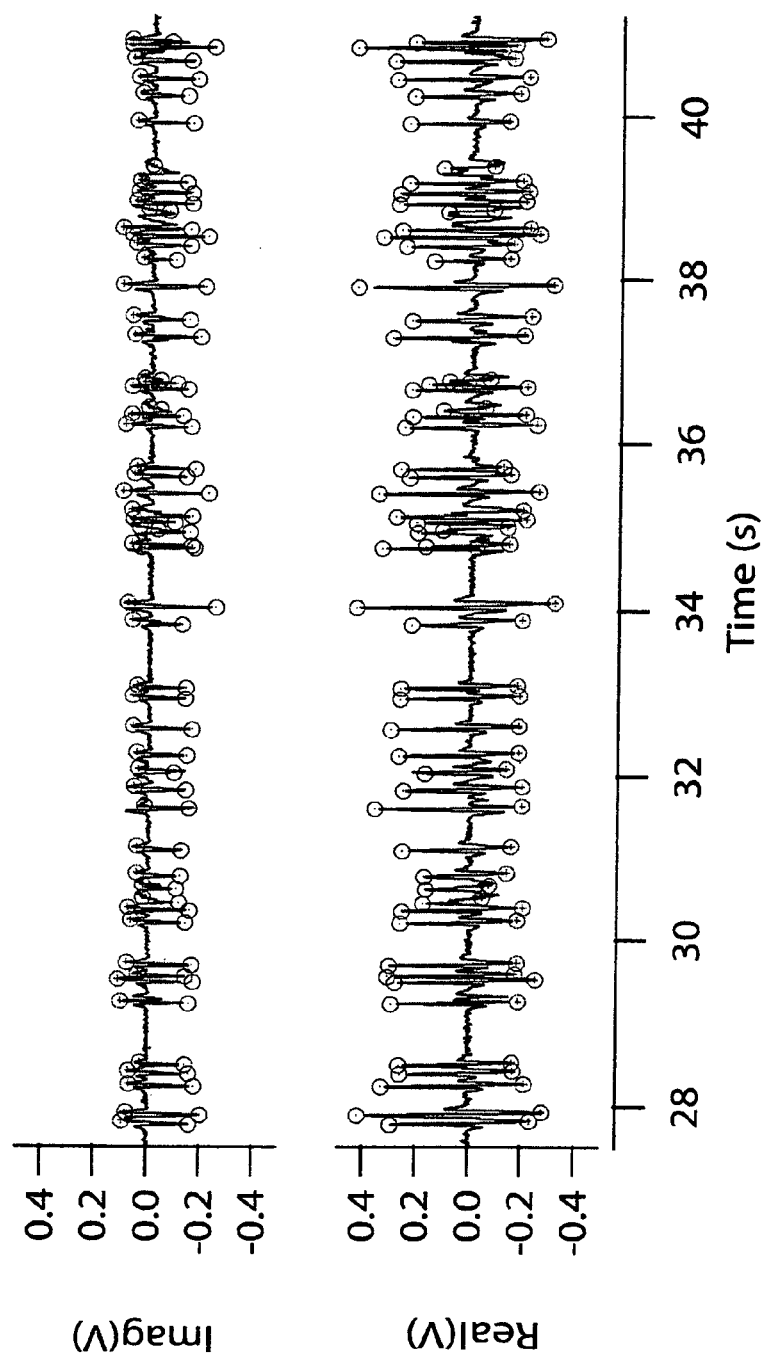
FIG. 21 is a plot of time-based data collected during electrical interrogation of a sensor structured according to certain principles of the instant invention as a whole blood sample is interrogated.

FIG. 21 illustrates the real and imaginary components of voltage measured at a measurement electrode using a 100 kHz interrogation frequency. The plotted traces in FIG. 21 were high-pass filtered.

Figure 22:
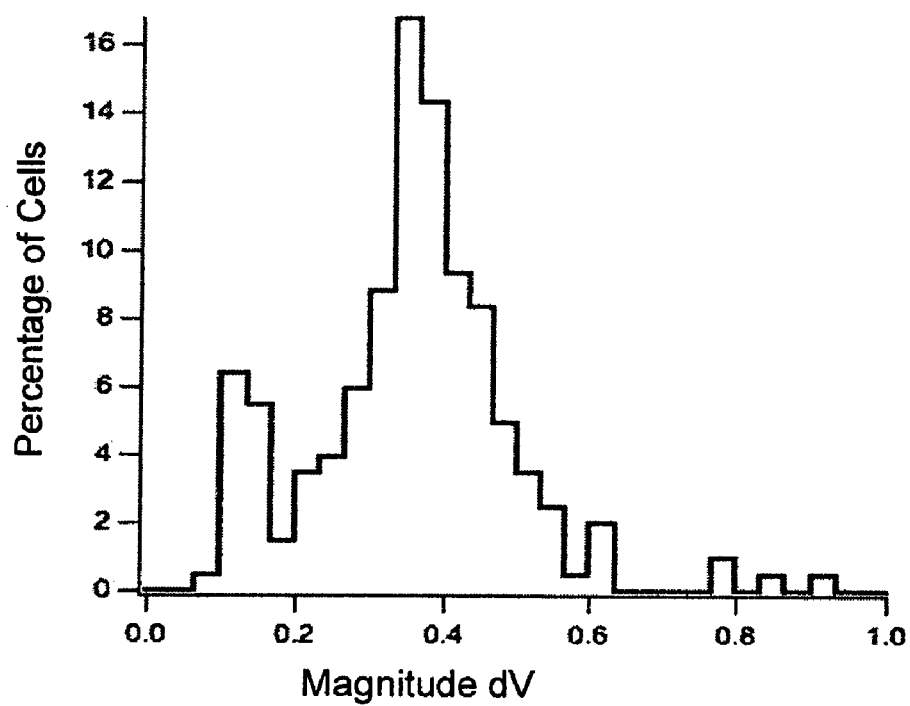
FIG. 22 is a distribution plot showing data collected from interrogation of a sensor during a short run of a polydisperse suspension of whole blood cells.

FIG. 22 is a distribution plot (showing the percentages of total cells counted in each horizontal axis bin), for a short run of a polydisperse suspension of blood cells using a 25 μm interrogation channel through a three-electrode thin film sensor. Preliminary data illustrate the ability to discriminate between platelets (left peak), red blood cells (large center peak), and white blood cells (small peaks on right).

While the invention has been described in particular with reference to certain illustrated embodiments, such is not intended to limit the scope of the invention. The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An electrically operated sensor including a thin film arrangement structured as a multilayer sandwich, the sensor comprising:
a first stimulated electrode providing an area disposed in a substantially planar configuration;
a first measurement electrode providing an area disposed in approximately parallel proximity to said first stimulated electrode;
a second stimulated electrode providing an area disposed in approximately parallel proximity to said first measurement electrode, and on an opposite side of said first measurement electrode from said first stimulated electrode;
a first electrically insulating layer disposed between said first stimulated electrode and said first measurement electrode to resist electrical communication there-between;
a second electrically insulating layer disposed between said first measurement electrode and said second stimulated electrode to resist electrical communication there-between; and
a first channel providing a fluid flow path through said first stimulated electrode, said first insulating layer, said first measurement electrode, said second insulating layer, and said second stimulated electrode, and permitting electrolytic electrical communication between said first stimulated electrode, said first measurement electrode, and said second stimulated electrode to form a first interrogation zone disposed between said first stimulated electrode and said second stimulated electrode; wherein:
said first stimulated electrode and said second stimulated electrode reside on layers of said sandwich; and
said first channel is structured and arranged to resist fluid flow in a direction parallel to said area of said first measurement electrode.

2. The sensor according to claim 1, wherein:
a thickness of said first insulating layer is less than about 0.01 inches;
a thickness of said second insulating layer is less than about 0.01 inches;
a characteristic size of said first channel is between about 3 and 150 microns; and
a thickness of each of said first stimulated electrode, said first measurement electrode, and said second stimulated electrode is sized less than about 100 microns.

3. The sensor according to claim 1, further comprising:
a second measurement electrode disposed between said first insulating layer and said second insulating layer to provide an area disposed in approximately parallel proximity to said first stimulated electrode; and
a second channel providing a fluid flow path through said first stimulated electrode, said first insulating layer, said second measurement electrode, said second insulating layer, and said second stimulated electrode, said second channel having a characteristic size between about 2 and 150 microns and permitting electrolytic electrical communication between said first stimulated electrode, said second measurement electrode, and said second stimulated electrode to form a second interrogation zone disposed between said first stimulated electrode and said second stimulated electrode; wherein:
said first channel and said second channel define respective first and second independent flow paths structured to resist commingling of fluids flowing therein.

4. The sensor according to claim 1, further comprising:
a plurality of individually addressable measurement electrodes disposed in sandwich relation between said first stimulated electrode and said second stimulated electrode, said plurality of measurement electrodes being substantially electrically independent from each other, and each associated with a cooperating channel that defines an independent fluid path through said first stimulated electrode and the respective measurement electrode, to form a plurality of parallel interrogation zones disposed between said first stimulated electrode and said second stimulated electrode.

5. The sensor according to claim 1, wherein:
an entrance to said first channel is structured to form a metering aperture.

6. The sensor according to claim 1, wherein:
wall structure of said first channel is arranged to form a metering aperture.

7. The sensor according to claim 1, wherein:
said sensor is structured and arranged to permit electrical communication between selected electrodes and cooperating probe structure of an interrogation platform by way of electrical contact pads disposed for access by said probe structure from a single side of said sensor.

8. The sensor according to claim 7, wherein:
said sensor comprises an electrically conductive via disposed between a contact pad and its associated electrode, said via passing through at least one insulation layer.

9. The sensor according to claim 7, wherein:
said sensor is structured and arranged to provide access for a probe structure of an interrogation platform, to a connector contact pad associated with an electrode, through a window formed through an insulating layer.

10. The sensor according to claim 1, wherein:
said sensor is structured and arranged to provide a plurality of sensor zones disposed for parallel interrogation of a fluid sample.

11. The sensor according to claim 1, wherein:
said sensor is structured and arranged to provide a plurality of sensor zones disposed for serial interrogation of a portion of a fluid sample.

12. The sensor according to claim 1, wherein:
said first and second stimulated electrodes are affixed to separate insulation layers.

13. The sensor according to claim 1, wherein:
a stimulated electrode and a measurement electrode are affixed to opposite sides of one insulator layer.

14. The sensor according to claim 4, wherein:
a stimulated electrode is affixed to an opposite side of one insulator layer from a plurality of measurement electrodes.

15. The sensor according to claim 1, wherein:
insulating layers include alignment structure adapted to urge alignment of constituent layers during assembly of the sensor.

16. The sensor according to claim 1, further in combination with:
a cartridge comprising a sample input aperture in fluid communication through said sensor to a waste reservoir, said cartridge being configured and arranged to present contact pads associated with said sensor for electrical communication with electrical interrogation circuitry.

17. The sensor according to claim 16, wherein:
said cartridge is adapted for one-time, disposable use.

18. The sensor according to claim 16, further in combination with:
an interrogation platform comprising:
probe structure effective to form an electrical communication between said electrodes and electronic interrogation circuitry;
a motive source to cause fluid transport through said sensor; and
alignment structure to assist in engagement of said cartridge in repeatable and operable position with respect to said platform.

19. The sensor according to claim 1, further comprising:
a third stimulated electrode providing an area disposed in a substantially planar configuration;
a second measurement electrode providing an area disposed in approximately parallel proximity to said third stimulated electrode;
a fourth stimulated electrode providing an area disposed in approximately parallel proximity to said second measurement electrode, and on an opposite side of said second measurement electrode from said third stimulated electrode;
a second channel providing a fluid flow path through said third stimulated electrode, said first insulating layer, said second measurement electrode, said second insulating layer, and said fourth stimulated electrode, and permitting electrolytic electrical communication between said third stimulated electrode, said second measurement electrode, and said fourth stimulated electrode to form a second interrogation zone associated with said sandwich; wherein:
said second channel is structured and arranged to resist fluid flow in a direction parallel to said area of said second measurement electrode.

20. A method for analyzing particles suspended in a fluid, comprising the steps of:
a) adding a known volume of particle-containing fluid to a one-time use disposable cartridge comprising a thin film sensor;
b) providing a sandwich type thin film sensor having an at least first and second planar stimulating electrodes, and at least one planar measuring electrode situated therebetween, allowing fluid flow in at least one interrogation channel transversely through said sandwich type thin film sensor;
c) inserting said cartridge into a docking port of an interrogation platform;
d) causing a pressure differential across said thin film sensor effective to move said fluid through said sensor;
e) analyzing particles flowing through said sensor by monitoring changes in electric impedance as said particles flow through said one or more interrogation channels; and
f) displaying analysis results on a display screen of said platform.

21. An electrically operated sensor including a thin film arrangement structured as a multilayer sandwich, the sensor comprising:
a first stimulated electrode providing an area disposed in a substantially planar configuration;
a first measurement electrode providing an area disposed in approximately parallel proximity to said first stimulated electrode;
a second stimulated electrode providing an area disposed in approximately parallel proximity to said first measurement electrode, and on an opposite side of said first measurement electrode from said first stimulated electrode;
a first electrically insulating layer disposed between said first stimulated electrode and said first measurement electrode to resist electrical communication there-between;
a second electrically insulating layer disposed between said first measurement electrode and said second stimulated electrode to resist electrical communication there-between; and
a first channel providing a fluid flow path through said first stimulated electrode, said first insulating layer, said first measurement electrode, said second insulating layer, and said second stimulated electrode, and permitting electrolytic electrical communication between said first stimulated electrode, said first measurement electrode, and said second stimulated electrode; wherein:
a top surface of said first measurement electrode is affixed to a bottom surface of said first insulating layer and a bottom surface of said first measurement electrode is affixed to a top surface of said second insulating layer.

* * * * *